(12) United States Patent
Chiu et al.

(10) Patent No.: US 8,013,194 B2
(45) Date of Patent: Sep. 6, 2011

(54) PROCESS FOR THE MANUFACTURE OF FLUORINATED OLEFINS

(75) Inventors: Yuon Chiu, Denville, NJ (US); Stephen A. Cottrell, Baton Rouge, LA (US); Hsueh Sung Tung, Getzville, NY (US); Haluk Kopkalli, Staten Island, NY (US); Gustavo Cerri, Parsippany, NJ (US)

(73) Assignee: Honeywell International Inc., Morristown, NJ (US)

( * ) Notice: Subject to any disclaimer, the term of this patent is extended or adjusted under 35 U.S.C. 154(b) by 118 days.

(21) Appl. No.: 12/402,372

(22) Filed: Mar. 11, 2009

(65) Prior Publication Data
US 2009/0234165 A1 Sep. 17, 2009

Related U.S. Application Data

(60) Provisional application No. 61/036,526, filed on Mar. 14, 2008.

(51) Int. Cl.
*C07C 17/00* (2006.01)
(52) U.S. Cl. .......... 570/155; 570/156; 570/175
(58) Field of Classification Search .......... 570/155, 570/156, 175
See application file for complete search history.

(56) References Cited

U.S. PATENT DOCUMENTS

| | | | |
|---|---|---|---|
| 5,396,000 | A | 3/1995 | Nappa et al. |
| 5,679,875 | A | 10/1997 | Aoyama et al. |
| 6,031,141 | A | 2/2000 | Mallikarjuna et al. |
| 6,548,719 | B1 | 4/2003 | Nair et al. |
| 2006/0106263 | A1 | 5/2006 | Miller et al. |
| 2007/0123741 | A1 | 5/2007 | Van Der Puy et al. |
| 2007/0129579 | A1 | 6/2007 | Wang et al. |

FOREIGN PATENT DOCUMENTS

| | | |
|---|---|---|
| EP | 0982281 | 3/2000 |
| WO | 98/33755 | 8/1998 |
| WO | 2007117391 | 10/2007 |

*Primary Examiner* — Jafar Parsa
(74) *Attorney, Agent, or Firm* — Bruce Bradford

(57) ABSTRACT

A method for producing 1,1,1,2-tetrafluoropropene and/or 1,1,1,2,3-pentafluoropropene using a single set of four unit operations, the unit operations being (1) hydrogenation of a starting material comprising hexafluoropropene and optionally recycled 1,1,1,2,3-pentafluoropropene; (2) separation of the desired intermediate hydrofluoroalkane, such as 1,1,1,2,3,3-hexafluoropropane and/or 1,1,1,2,3-pentafluoropropane; (3) dehydrofluorination of the intermediate hydrofluoroalkane to produce the desired 1,1,1,2-tetrafluoropropene and/or 1,1,1,2,3-pentafluoropropene, followed by another separation to isolate the desired product and, optionally, recycle of the 1,1,1,2,3-pentafluoropropene.

8 Claims, 6 Drawing Sheets

_US 8,013,194 B2_

PROCESS FOR THE MANUFACTURE OF FLUORINATED OLEFINS

CROSS-REFERENCES TO RELATED APPLICATIONS

This application is related to and claims the priority benefit of U.S. Provisional Patent Application No. 61/036,526, filed Mar. 14, 2008, which is incorporated herein by reference. Also incorporated herein by reference are U.S. patent application Ser. Nos. 11/588,465 and 11/588,671, both of which were filed on Oct. 27, 2006.

BACKGROUND OF THE INVENTION

Fluorinated olefins, as a class, have many and varied uses, including as chemical intermediates and monomers, refrigerants, blowing agents, propellants and solvents.

Several methods for preparing fluorinated olefins are known. For example, U.S. Pat. No. 5,679,875 discloses methods for manufacturing 1,1,1,2,3-pentafluoropropene and 1,1,1,2,3-pentafluoropropane; U.S. Pat. No. 6,031,141 discloses a catalytic process using chromium-containing catalysts for the dehydrofluorination of hydrofluorocarbons to fluoroolefins; U.S. Pat. No. 5,396,000 discloses a process for producing CF3CHFCH2F using vapor phase catalytic dehydrohalogenation to produce CF3CF=CHF and HF, followed by vapor phase catalytic hydrogenation of CF3CF=CHF in the presence of HF; U.S. Pat. No. 6,548,719 discloses a process for producing fluoroolefins by dehydrohalogenating a hydrofluorocarbon in the presence of a phase transfer catalyst; U.S. Publication No. 2006/0106263 discloses the production and purification of hydrofluoroolefins compounds; and WO98/33755 discloses catalytic process for the dehydrofluorination of hexafluoropropanes to pentafluoropropenes.

Applicants have also come to appreciate that 1,1,1,2,3-pentafluoropropene (HFO-1225ye) and 1,1,1,2-tetrafluoropropene (HFO-1234yf) are each useful in various application, and in certain application, one of the compounds might be favored over the other. For example, HFO-1234yf is more preferred than HFO-1225ye for certain refrigerant and blowing agent applications.

Applicants have previously developed a process for producing HFO-1234yf which involves hydrogenating HFO-1225ye to produce 1,1,1,2,3-pentafluoropropane (HFC-245eb) and then using the HFC-245eb as a reactant in a dehydrofluorination reaction to produce HFO-1234ye. Applicants have also previously developed a process for producing HFO-1225ye which involves first hydrogenating hexafluoropropylene (HFP) to produce 1,1,1,2,3,3-hexafluoropropane (HFC-236ea) and then using the HFC-236ea as a reactant in a dehydrogenation reaction to produce HFO-1225ye. To commercially produce these two products according to these prior art processes, a manufacturing facility would require a minimum of four separate unit operations for each product, i.e., hydrogenation of the starting material, separation of the desired intermediate, dehydrofluorination of the intermediate to produce the desired product, followed by another separation to isolate the desired product. Applicants have come to appreciate that substantial economic investment would be required to develop such a commercial facility. As a result, it might become economically prohibitive to build a processing facility to produce each of these desirable fluorinated olefins according to the prior art processes.

In view of applicants' recognition of the above-noted problems and features of prior processes, applicants have developed improved processes that are capable of achieving substantial economic advantage in capital cost as well as substantial flexibility and advantage in the actual operation to maximize efficiency and production of a range of fluorinated olefins.

SUMMARY OF THE INVENTION

Applicants have found that both HFO-1225ye and HFO-1234yf can be produced in a single facility having four unit operations. The present invention, in part, is the recognition that hydrogenation of HFP with hydrogen yields both HFC-236ea and HFC-245eb. (It is believed that the HFC-245eb forms from the reaction of HFC-236ea with $H_2$.) Like HFC-236ea, HFC-245eb subsequently can be dehydrofluorinated to produce a desirable product. In particular, HFC-236ea can be dehydrofluorinated to produce HFO-1225ye and HFC-245eb can be dehydrofluorinated to produce HFO-1234yf. Thus, both HFO-1225ye and HFO-1234yf can be produced using a single set of four unit operations: hydrogenation of the starting material, separation of the desired intermediate, dehydrofluorination of the intermediate to produce the desired product, followed by another separation to isolate the desired product. For example, in a preferred system, HFP and H2 are reacted in a hydrogenation reactor to form an intermediate product stream comprising HFC-236ea and/or HFC-245eb. The relative concentrations of HFC-236ea and HFC-245eb is dependant on reaction conditions in the hydrogenation reactor, such as pressure, temperature, and relative concentration of reactants in the reactor. If the desirable end product is HFO-1225ye, then processing conditions preferably favor the production of HFC-236ea. That is, the hydrogenation reactor is operated to produce an intermediate product stream rich in HFC-236ea which is subsequently separated from the intermediate process stream and fed into a dehydrofluorination reactor to form a final product stream comprising HFO-1225ye. This HFO-1225ye is then separated from the final product stream and recovered as a purified product. If the desirable end product is HFO-1234yf, then processing conditions preferably favor the production of HFC-245eb. That is, the hydrogenation reactor is operated to produce an intermediate product stream rich in HFC-245eb. This can be accomplished by operating the hydrogenation reactor under conditions favorable to convert the HFP into HFC-236ea and then converting the HFC-236ea into HFC-245eb. The HFC-245eb is then separated from the intermediate product stream and fed into a dehydrofluorination reactor to form a final product stream comprising HFO-1234yf. This HFO-1234yf is then separated from the final product stream and recovered as a purified product.

In addition, when HFO-1234yf is the desired product, HFO-1225ye can be introduced into the hydrogenation reactor at some point and then converted into HFC-245eb. The source of this HFO-1225ye can be either a separate feed stream and/or a recycle stream (i.e., recycling HFO-1225ye derived from HFC-236ea as noted above). The HFC-245eb is again separated from the intermediate product stream and fed into a dehydrofluorination reactor to form a final product stream comprising HFO-1234yf. This HFO-1234yf is then separated from the final product stream and recovered as a purified product.

The discovery that both HFO-1225ye and HFO-1234yf can be produced using the same processing equipment is of great economic advantage. Accordingly, the present invention provides in one aspect methods of producing fluorinated olefins, preferably fluorinated olefins having from 3 to 6 carbon atoms and at least 4 fluorine substituents, and even more preferably at least one fluorinated olefin selected from the group consisting of 1,1,1,2-tetrafluoropropene (HFO-1234yf), 1,1,1,2,3-pentafluoropropene (HFO-1225ye) and combinations of these. The methods preferably comprise: hydrogenating at least one highly fluorinated olefin, preferably a fluorinated propene having a degree of fluorination of N+1, and even more preferably at least five fluorine substituents (i.e., N=4 or greater), and even more preferably HFP, to produce one or more fluorinated alkanes, preferably one or more fluorinated propanes having a degree of fluorination of N+1, even more preferably HFC-236ea and/or HFC-245eb; and dehydrofluorinating the fluorinated alkane(s) to produce a crude product stream comprising one or more of the desired fluorinated olefins having a degree of fluorination of N, preferably HFO-1234yf and/or HFO-1225ye. In preferred applications, these methods further comprise the step of providing a separation system capable of separating from the crude product stream a first desired fluorinated olefin and further providing at least a first and a second alternative flow path for said first fluorinated olefin, said first flow path being adapted to introduce (e.g., recycle) at least a portion of said first fluorinated olefin into said hydrogenation reaction step and said second flow path being adapted to deliver said first desired fluoroolefin to further processing to produce a relatively refined product stream containing said first desired fluoroolefin, said first and second alternate flow paths being operable independently.

Referring to FIG. 10, another aspect of the present invention provides systems capable of simultaneously and alternatively producing 1,1,1,2-tetrafluoropropene (HFO-1234yf) and 1,1,1,2,3-pentafluoropropene (HFO-1225ye) comprising: (a) at least a first hydrogenation reactor adapted to be operated under conditions effective to convert a feed stream comprising HFP, and optionally or alternatively HFO-1225ye, into at least one hydrogenation reaction product stream comprising a major proportion of HFC-236ea or a major proportion of HFC-245eb (based on the total amount of HFC-236ea and HFC-245eb in the hydrogenation reaction product stream); (b) at least a first separator capable of separating said hydrogenation reactor product stream into a plurality of streams, wherein at least one of said streams (i.e., a first intermediate stream) is relatively rich in either HFC-236ea or HFC-245eb and, optionally, another stream (i.e., a second intermediate stream) relatively rich in the other; (c) at least one dehydrofluorination reactor adapted to be operated under conditions effective to convert at least a portion of the hydrogenation reaction product separated into said first and/or second intermediate streams into at least one of 1,1,1,2-tetrafluoropropene (HFO-1234yf), 1,1,1,2,3-pentafluoropropene (HFO-1225ye), and combinations of these. In preferred embodiments, the systems further comprise: (d) at least a second separator capable of separating dehydrofluorination reaction product into at least a first product stream relatively rich in HFO-1234yf and/or at least a second product stream relatively rich in HFO-1225ye. In certain preferred embodiments the systems include a flow path for recycling at least a portion, and preferably all, of the stream rich in HFO-1225ye to the hydrogenation reactor and a flow path. In certain preferred embodiments, the systems include at least a second flow path operable simultaneously and independently of said first flow path to deliver said HFO-1225ye to further processing to produce a relatively refined product stream containing relatively higher concentrations of HFO-1225ye.

DETAILED DESCRIPTION

Figure 1:
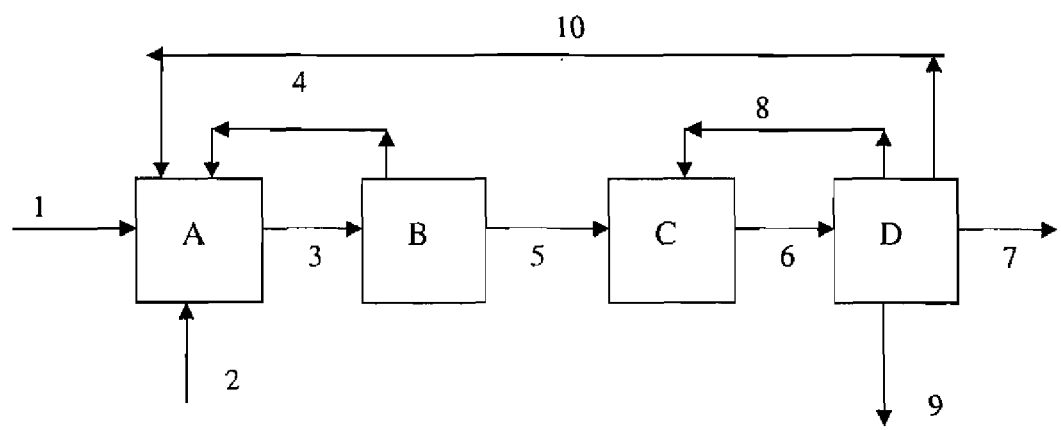
FIG. 1 is a process flow diagram showing the production of fluoroolefins according to an embodiment of the invention.

In certain highly preferred embodiments, the desired fluorinated olefins of the present invention comprise one or more C3 to C6 fluoroalkenes, preferably compounds having a formula as follows:

$X^1CF_zR_{3-z}$ where $X^1$ is a C2, C3, C4, or C5 unsaturated, substituted or unsubstituted, alkyl radical, each R is independently C1, F, Br, I or H, and z is 1 to 3. Highly preferred among such compounds are propenes and butenes having from 3 to 5 fluorine substituents, and among these tetrafluoropropenes (HFO-1234) and pentafluoropropenes (HFO-1225) are especially preferred.

Preferred processes of the present invention comprise reacting a fluorinated olefin starting material with a degree of halogen substitution of N+1 having substantially the same number of carbon atoms as the fluorinated olefin(s) to be synthesized with a degree of halogen substitution of N. Preferably the fluorinated olefin starting material having a degree of fluorine substitution of N+1 is exposed to reaction conditions effective to produce a reaction product containing one or more fluorinated alkanes having the same number of carbons atoms as the olefin. In one preferred aspect of the present invention, this olefin conversion step comprises a reaction that is sometimes referred to herein for convenience, but not necessarily by way of limitation, as a reduction or hydrogenation step. The fluorinated alkane is then preferably converted to a fluorinated olefin having a degree of fluorine substitution of N. In one preferred aspect of the present invention, this alkane conversion step comprises a reaction that is sometimes referred to herein for convenience, but not necessarily by way of limitation, as a dehydrohalogenation reaction or more particularly in certain embodiments as a dehydrofluorination or dehydrochlorination reaction.

According to one aspect of the present invention, the present processes preferably comprise the steps of
 (a) hydrogenating a compound of formula (I)

$$(CX_nY_{3-n})(CR^1_aR^2_b)_zCX=CH_mX_{2-m} \quad (I)$$

under conditions effective to form at least one fluorinated alkane of formula (II)

$$(CX_nY_{3-n})(CR^1_aR^2_b)_zCHXCH_{m+1}X_{2-m} \quad (II)$$

where:
each X is independently Cl, F, I or Br, provided that at least two Xs are F;
each Y is independently H, Cl, F, I or Br;
each $R^1$ is independently H, Cl, F, I, Br or unsubstituted or halogen substituted methyl or ethyl radical;
each $R_2$ is independently H, Cl, F, I, Br or unsubstituted or halogen substituted methyl or ethyl radical;
n is 1, 2 or 3 (preferably 3);
a and b are each 0, 1 or 2, provided that a+b=2;
m is 0, 1 or 2 (preferably 0 or 1); and
z is 0, 1, 2 or 3 (preferably 0), and
 (b) deydrohalogenating the compound of formula (II) under conditions effective to produce a fluoroolefin with a lower degree of fluorine substitution than the compound of formula (I), preferably to produce a compound of formula (III):

$$(CX_nY_{3-n})(CR^1_aR^2_b)_ZCX=CH_{m+1}X_{1-m} \quad (III)$$

where each n is the same value as in formula (I) and m is 0 or 1.

In certain preferred embodiments, the reactant of formula (I) comprises a three carbon olefin of formula (IA) wherein z is 0, namely $$CX_nY_{3-n}CX=CH_mX_{2-m} \quad (IA)$$

to produce a three carbon alkane of formula (IIA) as follows:

$$(CX_nY_{3-n})CHXCH_{m+1}X_{2-m} \quad (IIA)$$

where X, Y, n, and m are all as indicated above, which compound is then dehydrohalogenated to form a compound of formula (IIIA)

$$(CX_nY_{3-n})CX=CH_{m+1}X_{1-m} \quad (IIIA)$$

where n is the same value as in formula (IA) and m is 0 or 1.

In certain highly preferred aspects of such embodiments, a saturated terminal carbon of the compounds of formulas (I) or (IA) is fully substituted with fluorine (for example, n on the saturated terminal carbon is 3 and each X on that carbon is F), and even more preferably n is 3 and each X in the compound is F.

For three carbon embodiments of such preferred aspects, the compound of Formula (IA) is preferably a fluoropropene having from three to six fluorine substituents, and potentially other halogen substituents, including for example hexafluoropropene (that is, Z is 0, n is 3, m is 0, and all X are F) or pentafluoropropene (that is, Z is 0, n is 3, m is 1, and all X are F), and the compound of formula (IIA) preferably comprises, and more preferably is selected from the group consisting of, one or more of the following fluorinated alkanes: chlorotrifluoropropane (HCFC-244) and pentafluoropropane (HFC-245), and hexafluoropropane (HFC-236), including all isomers of each of these, but preferably 1,1,1,2,3-pentafluoropropane (HFC-245eb), 1,1,1,2,3,3-hexafluoropropane (HFC-236ea) and combinations of these. In certain preferred embodiments the fluorinated alkane produced by the conversion step has a degree of fluorine substitution of N+1.

In preferred embodiments, the step wherein the olefin is converted to an alkane is carried out under conditions effective to provide a formula (I) conversion of at least about 40%, more preferably at least about 55%, and even more preferably at least about 70%. In certain preferred embodiments the conversion is at least about 90%, and more preferably about 99%. Further in certain preferred embodiments, the conversion of the compound of formula (I) to produce a compound of formula (II) is conducted under conditions effective to provide a formula (II) selectivity of at least about 60%, more preferably at least about 80%, and more preferably at least about 90%, and even more preferably about 100%.

In preferred embodiments, the step wherein the alkane is converted to a fluorinated olefin having a degree of fluorination of N is carried out under conditions effective to provide a formula (II) conversion of at least about 40%, more preferably at least about 55%, and even more preferably at least about 70%. In certain preferred embodiments the conversion is at least about 90%, and more preferably about 95%. Further in certain preferred embodiments, the conversion of the compound of formula (II) to produce a compound of formula (III) is conducted under conditions effective to provide a formula (III) selectivity of at least about 60%, more preferably at least about 80%, and more preferably at least about 90%, and even more preferably about 98%.

With reference now to FIG. 1, the preferred methods and systems of the present invention comprise at least a first hydrogenation reactor A and at least a first feed stream 1 to the hydrogenation reactor which comprises at least one fluorinated olefin having a degree of halogen substitution, and preferably a degree of fluorine substitution, of N+1. The hydrogenation step A preferably involves also a feed stream 2 comprising a reducing agent. The converting step A preferably includes providing one or more reaction vessels, at least one of which preferably contains a reduction or hydrogenation catalyst, and introducing streams 1 and 2 into the vessel(s) under conditions effective to achieve the desired conversion.

Although the streams 1 and 2 in the figure are shown for convenience as being separate streams, this is done for convenience and the present invention is not so limited. For example, the streams 1 and 2 could in certain embodiments be combined outside the vessel and then introduced to the vessel together, or in other embodiments stream 1 and stream 2 might each comprise several separate streams, each of which is introduced into the vessel(s) at different times and/or at different locations. Furthermore, the present invention contemplates, as will be described in more detail hereinafter, that the stream 1 may actually comprise two or more separate streams and the step A may comprise two or more reaction vessels. All such variations are contemplated. This same convention has been used and applies herein throughout to all use of the term "stream," "step" and the like in both the description and in the figures, unless specifically indicated otherwise.

The preferred converting step A produces at least one reaction product stream 3 which contains a fluorinated alkane in accordance with the present invention. Stream 3 is preferably introduced to a separation step B which provides at least a first stream 5 which is used as a reactant in the dehydrohalogenation step C. A stream or flow path 4 is also preferably provided from separation step B for returning at least a portion of the reaction product stream 3 to the hydrogenation reaction step A. Stream 5, which contains at least a portion of the fluorinated alkane reaction product form step A, is fed to the dehydrohalogenation step C, wherein the fluorinated alkane in stream is converted to a fluorinated olefin have a degree of halogen substitution, and in certain preferred embodiments fluorine substitution, of N in accordance with the present invention. The converting step C preferably includes providing one or more reaction vessels, at least one of which preferably contains a dehydrohalogenation catalyst and introducing at least stream 5 into the vessel(s) under conditions effective to produce the desired fluoroolefin in crude reaction product stream 6.

In preferred embodiments, the conversion step C produces a reaction product which includes not only one or more of the desired fluoroolefins, but also hydrogen and other by-products, which are withdrawn from the reaction step C by crude product stream 6. In such embodiments it is generally preferred to introduce the stream 6 into a separation step D in which at least a portion of the hydrogen is separated from the stream to produce at least a first stream 7 relatively rich (in comparison to the crude product stream 6) in the desired fluorinated olefin, at least a second stream relatively rich (in comparison to the feed stream 4) in hydrogen and/or other byproducts, and at least one recycle stream 8 for returning at least a certain portion of the unreacted reactants to the dehydrohalogenation step C. In addition, according to preferred embodiments, it is preferred to provide from the separation step or unit a flow path 10 for returning at least a portion of any HFO-1225ye contained in the crude reaction product 6 to the hydrogenation step A.

Preferred aspects of each of the steps A, B, C and D, and each of the feed streams, product streams and flow paths associated therewith are described below.

The Hydrogenation Step

Although it is contemplated that the hydrogenation or reduction step may be conducted in batch operation, it is preferred that the hydrogenation reaction is carried out as a substantially continuous operation. Furthermore, it is contemplated that the hydrogenation reaction may be conducted in a single reaction vessel, it is also contemplated that reaction step A may comprise two or more reactors or reaction stages in parallel, in series, or both, or any combination of reactor designs. In addition, it is contemplated that the reaction step may include one or more feed preheating steps or stages, depending on the particulars of each application.

While it is possible that the reaction may involve in certain embodiments a liquid phase reaction, it is contemplated that in preferred embodiments the hydrogenation reaction comprises, and even more preferably consists of, at least one vapor phase reaction stage.

Figure 2:
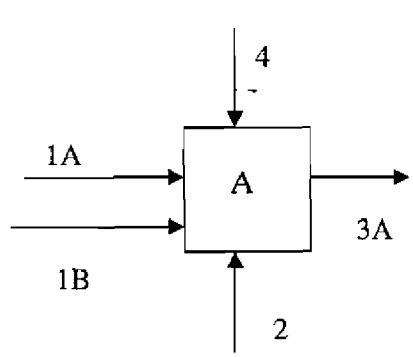
FIG. 2 is a process flow diagram showing the hydrogenation unit operation according to an embodiment of the invention.

In one preferred embodiment of the present invention, the hydrogenation step comprises a reaction step A having associated therewith at least a first flow path or feed stream 1A, at least a second flow path or feed stream 1B and at least a third flow path or feed stream 2, with each flow path being independently operable. One such embodiment is illustrated schematically in FIG. 2. In such embodiments, it is preferred that the first flow path or feed stream 1A comprises HFP and preferably substantially all of the HFP being fed to the reaction step A, the second path or feed stream 1B comprises HFO-1225ye, and preferably substantially all of the HFO-1225ye being fed to the reaction step A (it being recognized that the feed stream 1B in many embodiments will have a substantially zero flow and that in other embodiments this feed stream 1B may in fact be a recycle stream from subsequent operations in the process). The feed stream 2 comprises the hydrogenation agent, preferably H2, for the reaction step A. Flow path or stream 4 is at path for allowing introduction of a recycle stream into the reaction step. In some embodiments, the actual flow of recycle stream 4 is zero, but in preferred embodiments, the recycle stream comprises a relatively low temperature stream comprising a portion of the reaction product stream 3A after it has been cooled and separated, the content of recycle stream 4, when present, preferably being relatively rich in HFC-236ea, HFC-245eb, or a combination of these.

Figure 3:
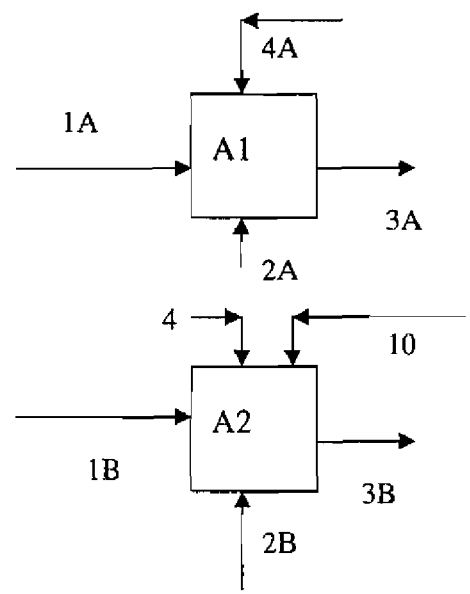
FIG. 3 is a process flow diagram showing the hydrogenation unit operation according to another embodiment of the invention.

In another preferred embodiment of the present invention as illustrated in FIG. 3, the hydrogenation step comprises at least a first reaction step A1 and a second reaction step A2. The first reaction step A1, which may comprise one or more reaction stages in parallel or in series or a combination of parallel or series, having associated therewith at least a first flow path or feed stream 1A and at least a second flow path or feed stream 2A, with each flow path being independently operable. The first reaction step A1, which may comprise one or more reaction stages in parallel or in series or a combination of parallel or series, having associated therewith at least a first flow path or feed stream 1A and at least a second flow path or feed stream 2A, with each flow path being independently operable. In such embodiments, it is preferred that the first flow path or feed stream 1A comprises HFP and preferably substantially all of the HFP being fed to the reaction step A, the second path or feed stream 2B comprises the hydrogenation agent, preferably H2, for the reaction step A. Flow path or stream 4A is at path for allowing introduction of a recycle stream into the reaction step. In some embodiments, the actual flow of recycle stream 4A is substantially zero, but in preferred embodiments, the recycle stream comprises a relatively low temperature stream comprising a portion of the reaction product stream 3A after it has been cooled and separated, the content of recycle stream 4, when present, preferably being relatively rich in HFC-236ea, HFC-245eb, or a combination of these. The first reaction step A1, which may comprise one or more reaction stages in parallel or in series or a combination of parallel or series, having associated therewith at least a first flow path or feed stream 1A and at least a second flow path or feed stream 2A, with each flow path being independently operable.

In connection with the reaction stage converting HFP in the hydrogenation reactor, it is preferred in certain embodiments to use a trickle bed reactor. It is contemplated that the reaction is such case proceeds as follows:

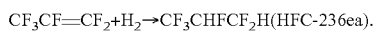

A major side reaction of this process yields HFC-245eb and HF. It is believed that 245eb is formed from 236ea by hydrodefluorination and/or by dehydrofluorination followed by reduction:

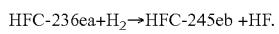

The second reaction step A2, which may comprise one or more reaction stages in parallel or in series or a combination of parallel or series, having associated therewith at least a first flow path or feed stream 1B and at least a second flow path or feed stream 2B, with each flow path being independently operable. In such embodiments, it is preferred that the first flow path or feed stream 2B, when present, comprises HFO-1225ye, and preferably substantially all of the HFO-1225ye being fed to the reaction step A (it being recognized that the feed stream 2B in many embodiments will have a substantially zero flow and that in other embodiments this feed stream 2B may in fact be a recycle stream from subsequent operations in the process). The second path or feed stream 2B comprises the hydrogenation agent, preferably H2, for the reaction step A2. Flow path or stream 4B is at path for allowing introduction of a recycle stream into the reaction step. In some embodiments, the actual flow of recycle stream 4B is zero, but in preferred embodiments, the recycle stream comprises a relatively low temperature stream comprising a portion of the reaction product stream 3A and/or 3B after it has been cooled and separated, the content of recycle stream 4B, when present, preferably being relatively rich in HFC-236ea, HFC-245eb, or a combination of these. Flow path or stream 10 is at path for allowing introduction of a second recycle stream into the reaction step, which in preferred embodiments comprises at least a portion of the reaction product stream 6 after being processed to comprise a stream relatively rich in HFO-1225ye.

In connection with the reaction stage converting HFO-1225ye in the hydrogenation reactor, it is preferred in certain embodiments to use a trickle bed reactor. It is contemplated that the reaction is such case proceeds as follows:

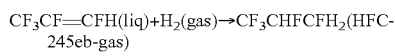
$CF_3CF=CFH(liq)+H_2(gas) \rightarrow CF_3CHFCFH_2(HFC\text{-}245eb\text{-}gas)$ A major side reaction is contemplated to be:

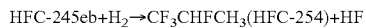
$HFC\text{-}245eb+H_2 \rightarrow CF_3CHFCH_3(HFC\text{-}254)+HF$

Preferably, the hydrogenation reaction conditions are controlled in the reaction in order to achieve the desired conversion and/or selectivity in accordance with the present invention. As used herein, the term "reaction conditions" is intended to include the singular and means control of any one or more processing parameters, including possibly using or not using a reaction vessel or stage, which can be modified by the operator of the reaction to produce the conversion and/or selectivity of the feed material in accordance with the teachings contained herein. By way of example, but not by way of limitation, conversion of the feed material may be controlled or regulated by controlling or regulating any one or more of the following: the temperature of the reaction, the flow rate of the reactants, the presence of diluent, the amount of catalyst present in the reaction vessel, the shape and size of the reaction vessel, the pressure of the reaction, and any one combinations of these and other process parameters which will be available and known to those skilled in the art in view of the disclosure contained herein. The size and shape, and other characteristics of the reaction vessel itself may vary widely with the scope of the present invention, and it is contemplated that the vessel associated with each stage may be different than or the same as the vessel associated with the upstream and downstream reaction stages. Furthermore, it is contemplated that all reaction stages can occur inside a single vessel, provided that means and mechanisms necessary to control conversion are provided. For example, it may be desirable in certain embodiments to utilize a single tubular reactor for each reaction stage, providing conversion control by judicious selection of the amount and/or distribution of catalyst throughout the tubular reactor. In such a case, it is possible to further control the conversion in different sections of the same tubular reactor by controlling the amount of heat removed from or added to different sections of the tubular reactor.

Those skilled in the art will be readily able to select the type of catalyst(s) used for the hydrogenation step of the present invention in view of the teachings contained herein. For example, it is preferred in certain embodiments that at least one, but preferably all, reaction stages utilize palladium catalyst, preferably 1% palladium on carbon, either alone or in combination with other catalysts. In this regard one or more of the hydrogenation catalyst disclosed in U.S. Pat. No. 5,679,875, which is incorporated herein by reference, may be used for one or more of the reaction stages in accordance with the present invention. In certain preferred embodiments, the catalyst preferably comprises palladium supported on carbon, such as a carbon mesh.

Thus, certain embodiments of the present methods comprise bringing a fluorinated olefin in accordance with formula I and a hydrogenation agent, such as $H_2$, into contact with a first amount of catalyst in at least a first reaction stage to produce a reaction stream comprising hydrofluorocarbon(s), unreacted fluorinated olefin and hydrogen. In certain preferred embodiments the hydrogenation step is followed by a preferred separation step as described below. While it is contemplated that a wide variety of hydrogenation reaction temperatures may be used, depending on relevant factors such as the catalyst being used and the most desired reaction product, it is generally preferred that the reaction temperature for the hydrogenation step is from about 50° C. to about 150° C., preferably about from 75° C. to about 115° C., and even more preferably from about 90° C. to about 100° C.

In general it is also contemplated that a wide variety of reaction pressures may be used, depending again on relevant factors such as the specific catalyst being used and the most desired reaction product. The reaction pressure can be, for example, from about 100 psig to about 300 psig, preferably about from 150 psig to about 250 psig, and even more preferably about 200 psig.

Applicants have found, without being bound by or to any particular theory, that the use of a cooled recycle stream 4 in the hydrogenation reaction allows the feed materials to serve as a means for removing heat from the hydrogenation reaction. Since the reduction or hydrogenation reaction of the present invention is generally exothermic, and usually substantially exothermic, the use of such a recycle material has the effect in preferred embodiments of maintaining the reactor temperature below that which would exist if the recycle were not used, assuming all other process conditions were maintained the same.

It is contemplated that the amount of hydrogen used may vary widely. In preferred embodiments, the hydrogen is feed to the reaction step as a gas in a H2:olefin feed ratio of from about 1:1 to about 2:1, and even more preferably ratio of from about 1:1 to about 1.5:1, and even more preferably about 1.3:1.

The Hydrogenation Reaction Effluent Separation

Thus, in certain preferred embodiments, the present invention includes the step of cooling at least a portion reactor product stream to remove at least a portion of the heat of reaction. In many preferred embodiments, this cooling step is included as part of the preferred aspects of the separation step B, which are described in connection with FIGS. 4, 5 and 6 below. Preferably the ratio of cooled recycled reaction product to fresh feed is about 12:1, with the temperature of the recycle stream preferably being at about 50° C. to about 100° C., and even more preferably about 70° C. In addition, in order to help remove heat of reaction, it is preferred in certain embodiments to introduce the fresh feeds and/or the recycle feeds to the reaction in the liquid phase and allowing the heat of reaction to evaporate the liquid feed and/or the reaction products and withdrawing the reaction products in the gas phase.

Figure 4:
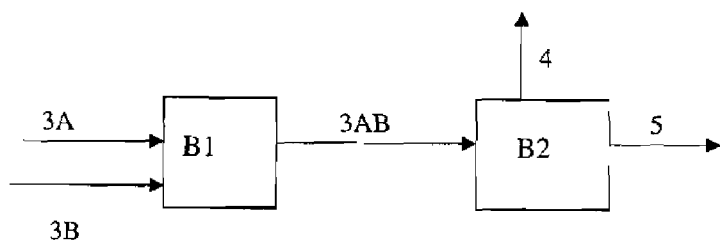
FIG. 4 is a process flow diagram showing the first separation unit operation according to an embodiment of the invention.

With reference now to FIG. 4, the reaction product streams 3A and 3B are directed to a separation step B, which comprises in the embodiment of FIG. 4 a cooling step B1 which produces one or more cooled reaction product streams 3AB, which in turn are fed to one or more separation stages B2. It is contemplated that those skilled in the art will be able to devise without undue experimentation many means and mechanisms for attaining such cooling in view of the teachings contained herein and all such means and mechanisms are with the scope of the present invention. The preferred separation step B2 preferably includes at least a first separation step which produces a first stream 4 relatively rich in unreacted hydrogen, fluorinated alkane, such as HFC-236ea and/or HFC-245eb, or a combination of these, which may be recycled, with or without further processing, to the reaction step A. A second stream 5, which is relatively rich in the fluorinated alkane, such as HFC-236ea and/or HFC-245eb, is also produced from the separation step B2.

Figure 4A:
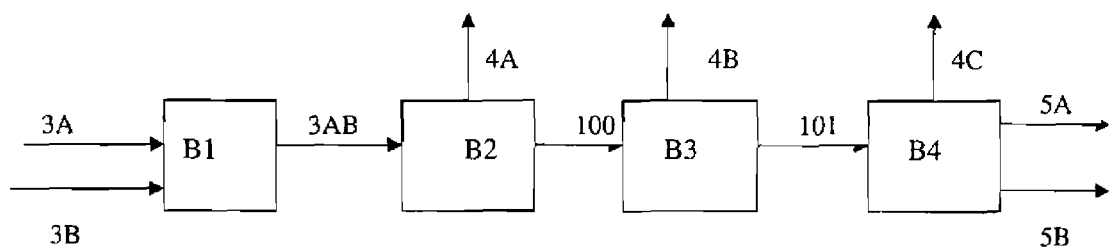

In one preferred embodiment shown in FIG. 4A, the separation step comprises, in addition to the cooling step B1 and the separation step B2 which produces at least a first cooled stream 4A containing a portion of the reaction product, which is preferably recycled to the reaction step A, and a crude product stream 100 which is fed to a further separation step B3 in which a substantial portion of excess hydrogen in the stream 100 is purged from the stream and sent for disposal or further processing in stream 4B. The stream 101 from the separation step B3 is then feed to a further separation step B4 where unwanted by-products are removed in stream 4C and one or more product streams 5A and 5B are produced. In preferred embodiments, stream 5A is relatively rich in a first fluorinated alkane, preferably HFC-236ea, and a second stream 5B rich in a second fluorinated alkane, preferably HFC-245eb.

Figure 5:
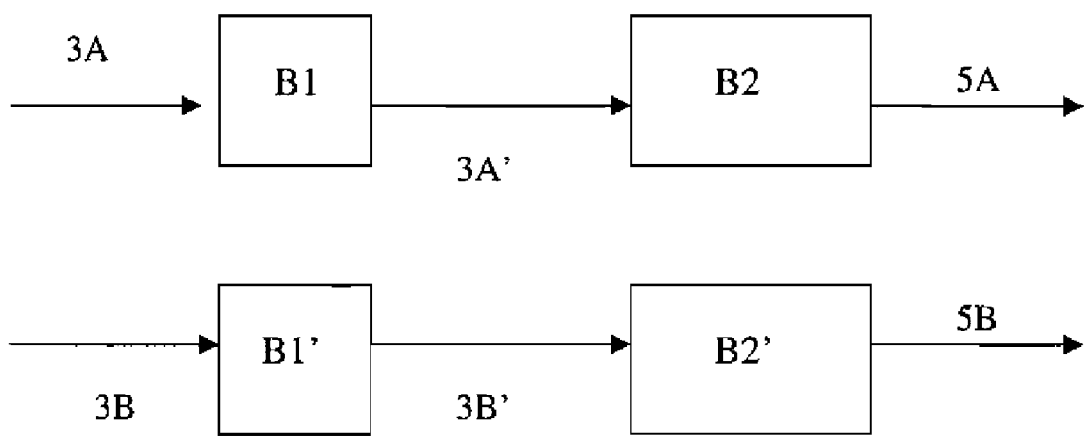
FIG. 5 is a process flow diagram showing the first separation unit operation according to another embodiment of the invention.
Figure 6:
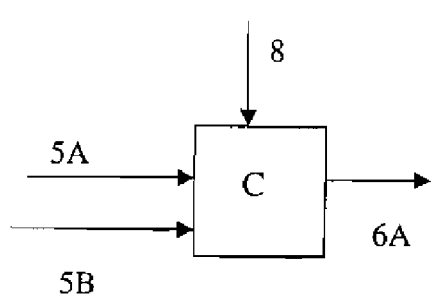
FIG. 6 is a process flow diagram showing the dehydrofluorination unit operation according to an embodiment of the invention.

In another embodiment described with reference now to FIG. 5, the reaction product streams 3A and 3B are each directed to a separate separation steps, which comprise separate cooling steps B1 and B1', each of which produces one or more cooled reaction product streams 3A' and 3B', which in turn are fed to separate separation stages B2 and B2' to produce a first stream 5A relatively rich in a first of the fluorinated alkane products, such as HFC-236ea when the feed stream 3A is rich in HFP, and a second reaction product stream 5B relatively rich in a second of the fluorinated alkane products, such as HFC-245eb when the feed stream 3B is rich in HFO-1225ye. A stream 4 (not shown) as described above in connection with FIG. 4 may also be removed from each of the steps B2 and B2'. In addition, the particular embodiments shown and described in FIG. 4A may also be adapted for use in connection with one or both the separation steps B and B' shown in FIG. 5.

Dehydrohalogenation

It is contemplated that the dehydrohalogenation reaction step may be preformed using a wide variety of process parameters and process conditions in view of the overall teachings contained herein, such as for example it is contemplated that the dehydrohalogenation step may comprise, in certain non-preferred embodiments, a liquid phase reaction. However, it is preferred in many embodiments of the present invention that this reaction step comprise a gas phase reaction, preferably in the presence of catalyst, preferably a metal catalyst, and even more preferably one or more transition metal-based catalysts (including in certain preferred embodiments transition metal halide catalysts), such as $FeCl_3$, chromiumoxyfluoride, Ni (including Ni mesh), $NiCl_2$, $CrF_3$, and mixtures thereof, supported or in bulk. Other catalysts include carbon-supported catalysts, antimony-based catalysts (such as $SbCl_5$), aluminum-based catalyst (such as $AlF_3$, $Al_2O_3$, and fluorinated $Al_2O_3$). It is expected that many other catalysts may be used depending on the requirements of particular embodiments, including for example palladium-based catalyst, platinum-based catalysts, rhodium-based catalysts and ruthenium-based catalysts. Of course, two or more any of these catalysts, or other catalysts not named here, may be used in combination.

In general it is preferred that the catalysts are fluorinated. In preferred embodiments, fluorination of the catalysts comprises exposing the catalyst to a stream of HF at about reaction temperature and pressure. The gas phase dehydrohalogenation reaction may be conducted, for example, by introducing a gaseous form of a compound of formula (II) into a suitable reaction vessel or reactor. Preferably the vessel is comprised of materials which are resistant to corrosion such as Hastelloy, Inconel, Monel and/or fluoropolymers linings. Preferably the vessel contains catalyst, for example a fixed or fluid catalyst bed, packed with a suitable dehydrohalogenation catalyst, with suitable means to heat the reaction mixture to the desired reaction temperature.

While it is contemplated that a wide variety of reaction temperatures may be used, depending on relevant factors such as the catalyst being used and the most desired reaction product, it is generally preferred that the reaction temperature for the dehydrohalogenation step is from about 150° C. to about 600° C., preferably about from 200° C. to about 400° C., and even more preferably from about 250° C. to about 300° C.

In general it is also contemplated that a wide variety of reaction pressures may be used, depending again on relevant factors such as the specific catalyst being used and the most desired reaction product. The reaction pressure can be, for example, superatmospheric, atmospheric or under vacuum. In certain embodiments, an inert diluent gas and/or an oxidizing agent, such as nitrogen, oxygen and mixture of nitrogen and oxygen, may be used in combination with the compound of formula (II) as a feed to the dehydrohalogenation step. When such a diluent and/or oxidizing agent is used, it is generally preferred that the feed streamed comprise formula (II) compound in an amount of from about 5% to greater than 95% by weight based on the combined weight of diluent and formula (II) compound.

It is contemplated that the amount of catalyst used will vary depending on the particular parameters present in each embodiment. In preferred embodiments, the contact time, which is expressed as the ratio of the volume of the catalyst (ml) to the total feed flow (ml/sec) is from about 0.1 seconds to about 1000 seconds, and preferably from about 2 seconds to about 120 seconds.

In general it is contemplated that the reaction is endothermic. To assist thermal management, it is contemplated in certain embodiments that the reactor comprises an isothermal tubular reactor, with heat input being provided by means of a relatively high temperature heating medium, such as hot salt and/or oil, superheated steam, or re-circulating hot gas. In addition, recycling of the HFO-1225ye produced in the reaction may be used to help control the temperature of the reaction.

One preferred dehydrohalogenation reaction comprises a dehydrofluorination reaction. For example, for embodiments in which the desired product of formula (III) is HFO-1234yf, it is preferred in certain embodiments that the compound of formula (II) comprises 1,1,1,2,3 pentafluoropropane. Applicants have found that in such embodiments it is preferred to use as the catalyst a fluorinated chromium oxide catalyst.

Preferably in such dehydrofluorination embodiments, the conversion is at least about 50%, more preferably at least about 65%, and even more preferably at least about 90%. Preferably, the selectivity to HFO-1234yf is at least about 70%, more preferably at least about 80% and more preferably at least about 90%. Preferably before each cycle of use, the dehydrohalogenation catalyst is dried, pre-treated and activated. It may also be advantageous in certain embodiments to periodically regenerate the catalyst after prolonged use while in place in the reactor. Pre-treatment may include heating the catalyst to about 250° C. to about 430° C. with a stream of nitrogen or other inert gas. The catalyst may then be activated by treating it with a stream of HF diluted with a large excess of nitrogen gas in order to obtain high catalyst activity.

Regeneration of the catalyst may be accomplished by any means known in the art such as, for example, by passing air or oxygen over the catalyst at temperatures of from about 100° C. to about 400° C. for from about 1 hour to about 3 days depending on the size of the reactor.

While it is possible that the reaction may involve in certain embodiments a liquid phase reaction, it is contemplated that in preferred embodiments the dehydrohalogenation reaction comprises, and even more preferably consists of, at least one vapor phase reaction stage. In one preferred embodiment of the present invention, the dehydrohalogenation step comprises a reaction step C having associated therewith at least a first flow path or feed stream 5A, at least a second flow path or feed stream 5B and at least a third flow path or feed stream 8, with each flow path being independently operable. One such embodiment is illustrated schematically in FIG. 6. In such embodiments, it is preferred that the first flow path or feed stream 5A comprises HFO-236ea and preferably substantially all of the HFO-236ea being fed to the reaction step C, the second path or feed stream 5B comprises HFC-245eb, and preferably substantially all of the HFO-245eb being fed to the reaction step C (it being recognized that the feed stream 5B in many embodiments will have a substantially zero flow). Flow path or stream 8 is at path for allowing introduction of a recycle stream into the reaction step. In some embodiments, the actual flow of recycle stream 8 is zero, but in preferred embodiments, the recycle stream comprises a relatively low temperature stream comprising a portion of the reaction product stream 6A after it has been cooled and separated, the content of recycle stream 4, when present, preferably being relatively rich in HFC-236ea, HFC-245eb, or a combination of these.

Figure 7:
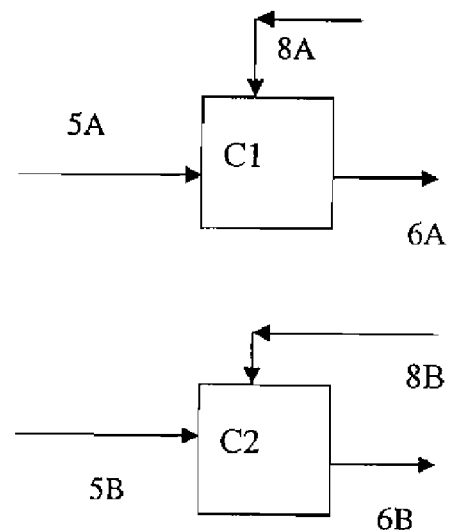
FIG. 7 is a process flow diagram showing the dehydrofluorination unit operation according to another embodiment of the invention.

In another preferred embodiment of the present invention as illustrated in FIG. 7, the dehydrohalogeantion step comprises at least a first reaction step C1 and a second reaction step C2. The first reaction step C1, which may comprise one or more reaction stages in parallel or in series or a combination of parallel or series, having associated therewith at least a first flow path or feed stream 5A and at least a second flow path or feed stream 8A, with each flow path being independently operable. The second reaction step C1, which may comprise one or more reaction stages in parallel or in series or a combination of parallel or series, having associated therewith at least a first flow path or feed stream 5B and at least a second flow path or feed stream 8B, with each flow path being independently operable. In such embodiments, it is preferred that the first flow path or feed stream 5A comprises HFO-236ea and preferably substantially all of the HFO-236ea being fed to the reaction step C, the second path or feed stream 5B comprises, when present, HFO-245eb and preferably substantially all of the HFO-245eb being fed to the reaction step C. Flow path or streams 8A and 8B are flow paths for allowing introduction of a recycle stream comprising at least a portion of unreacted feed back into the reaction step. In some embodiments, the actual flow of recycle streams 8A and 8B are substantially zero, but in preferred embodiments, the recycle streams comprises relatively low temperature streams comprising a portion of the reaction product streams 6A and 6B after they have been cooled and separated.

In connection with the reaction stage converting HFO-236ea in the dehydrohalogenation reactor, it is contemplated that the reaction is such case proceeds as follows:

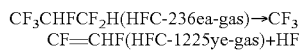

It will be appreciated that the present processes may include an isomerization step to convert to a desirable isomer of HFO-1225ye, which would typically be carried out at temperatures of about 150° C.

The second reaction step C2, which may comprise one or more reaction stages in parallel or in series or a combination of parallel or series, having associated therewith at least a first flow path or feed stream 5B and at least a second flow path or feed stream 8B, with each flow path being independently operable. In such embodiments, it is preferred that the first flow path or feed stream 5B comprises HFC-245eb, and preferably substantially all of the HFC-245eb being fed to the reaction step C. The second path or feed stream 8B comprises recycle of a portion of the reaction product, as described above.

In connection with the reaction stage converting HFC-245eb in the dehydrohalogenation reactor, it is contemplated that the reaction is such case proceeds as follows:

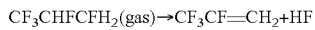

Preferably, the reaction conditions are controlled in the reaction in order to achieve the desired conversion and/or selectivity in accordance with the present invention. As used herein, the term "reaction conditions" is intended to include the singular and means control of any one or more processing parameters, including possibly using or not using a reaction vessel or stage, which can be modified by the operator of the reaction to produce the conversion and/or selectivity of the feed material in accordance with the teachings contained herein. By way of example, but not by way of limitation, conversion of the feed material may be controlled or regulated by controlling or regulating any one or more of the following: the temperature of the reaction, the flow rate of the reactants, the presence of diluent, the amount of catalyst present in the reaction vessel, the shape and size of the reaction vessel, the pressure of the reaction, and any one combinations of these and other process parameters which will be available and known to those skilled in the art in view of the disclosure contained herein. The size and shape, and other characteristics of the reaction vessel itself may vary widely with the scope of the present invention, and it is contemplated that the vessel associated with each stage may be different than or the same as the vessel associated with the upstream and downstream reaction stages. Furthermore, it is contemplated that all reaction stages can occur inside a single vessel, provided that means and mechanisms necessary to control conversion are provided. For example, it may be desirable in certain embodiments to utilize a single tubular reactor for each reaction stage, providing conversion control by judicious selection of the amount and/or distribution of catalyst throughout the tubular reactor. In such a case, it is possible to further control the conversion in different sections of the same tubular reactor by controlling the amount of heat removed from or added to different sections of the tubular reactor.

The Dehydrohalogenation Effluent Separation

As mentioned above, in addition to producing a fluorinated olefin, preferably fluorinated propene, the dehydrofluorination reaction also produces HF. In one preferred embodiment, HF is removed from the dehydrofluorination product stream by countercurrent extraction with sulfuric acid. In this embodiment, the product stream containing the HF is fed in one direction to a column, preferably a packed column. At the same time, a stream of sulfuric acid is fed, preferably countercurrently, to the same packed column. Appropriate column packing is readily determinable by one skilled in the art. Suitable column packing materials include those made of non-metallic polymeric materials, metals and alloys that are not reactive in the presence of HF or sulfuric acid, such as PTFE, PFA, hastelloy, monel, and noble metals. Preferably, the stream of sulfuric acid contains from about 50% to about 100% sulfuric acid, and more preferably about 80% sulfuric acid. In one embodiment, the stream of sulfuric acid is continuously fed to the top of the packed column at a feed rate of about twice the feed rate of the product stream, which in preferred embodiments is fed from the bottom of the packed column and moves in an generally upward direction substantially counter currently to the substantially down flowing stream containing the sulfuric acid. In certain embodiments, a stream comprising sulfuric acid and HF is removed from the bottom of the column and preferably at least a portion of the stream, and most preferably substantially all of the stream, is recycled back to the extraction tower. The recycling step is repeated preferably until the HF concentration in the column bottom is greater than about 10% by weight HF.

In one embodiment, the sulfuric acid and HF mixture containing greater than about 10% by weight HF is charged into a separate vessel. The mixture is then heated to a temperature sufficient to vaporize and flash of HF, which is collected. Another embodiment includes purifying the HF collected from the flash distillation.

Optionally, the HF or HCl generated from the dehydrohalogenation reaction is scrubbed from the product stream using water or caustic solutions.

In certain preferred embodiments, the present invention includes the step of cooling at least a portion reactor product stream to remove at least a portion of the heat of reaction. In many preferred embodiments, this cooling step is included as part of the preferred aspects of the separation step B, which are described in connection with FIGS. 4, 5, and 6 below. Preferably the ratio of cooled recycled reaction product to fresh feed is about 12:1, with the temperature of the recycle stream preferably being at about 50° C. to about 100° C., and even more preferably about 70° C. In addition, in order to help remove heat of reaction, it is preferred in certain embodiments to introduce the fresh feeds and/or the recycle feeds to the reaction in the liquid phase and allowing the heat of reaction to evaporate the liquid feed and/or the reaction products and withdrawing the reaction products in the gas phase.

Figure 8:
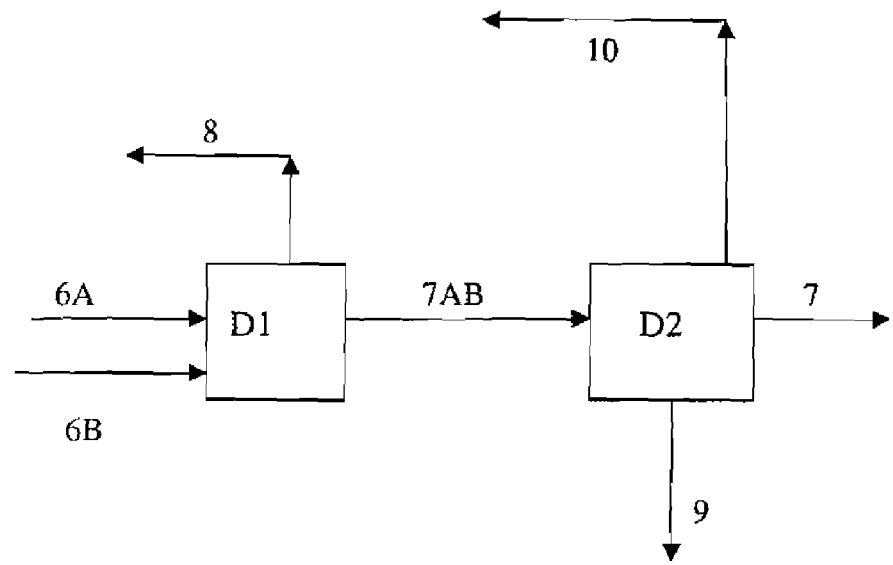
FIG. 8 is a process flow diagram showing the second separation unit operation according to an embodiment of the invention.

With reference now to FIG. 8, the reaction product streams 6A and 6B are directed to a separation step D, which comprises in the embodiment of FIG. 8 a cooling step D1 which produces one or more cooled reaction product streams 7AB, which in turn are fed to one or more separation stages D2. It is contemplated that those skilled in the art will be able to devise without undue experimentation many means and mechanisms for attaining such cooling in view of the teachings contained herein and all such means and mechanisms are with the scope of the present invention. The preferred separation step D2 preferably includes at least a first separation step which produces a first stream 8 relatively rich in unreacted fluorinated alkane, such as HFC-236ea and/or HFC-245eb, or a combination of these, which may be recycled, with or without further processing, to the reaction step C.

In one preferred embodiment shown in FIG. 8, the reaction product 7AB is separation step comprises a step for recovering any HF, preferably as described above, and a step for separating from the crude product stream unwanted by-product to produce a relatively purified product stream rich in HFO-1234yf, HFO-1225ye, or a separate stream rich in both. In certain embodiments, a portion of the HFO-1225ye may be separated from the product stream and recycled back to the hydrogenation reaction step and used as a feed thereto.

Figure 9:
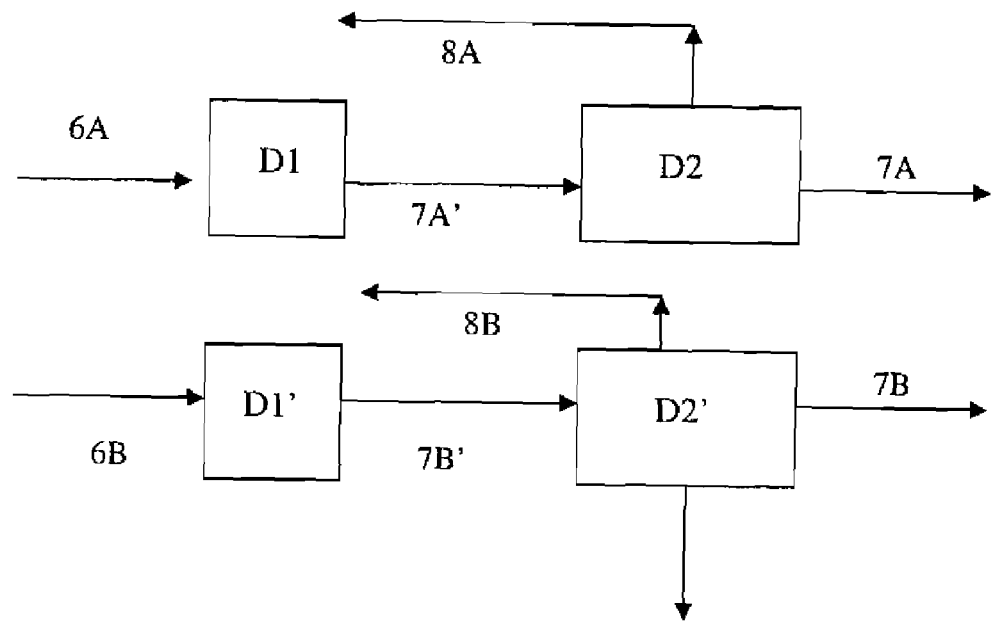
FIG. 9 is a process flow diagram showing the second separation unit operation according to another embodiment of the invention.
Figure 10:
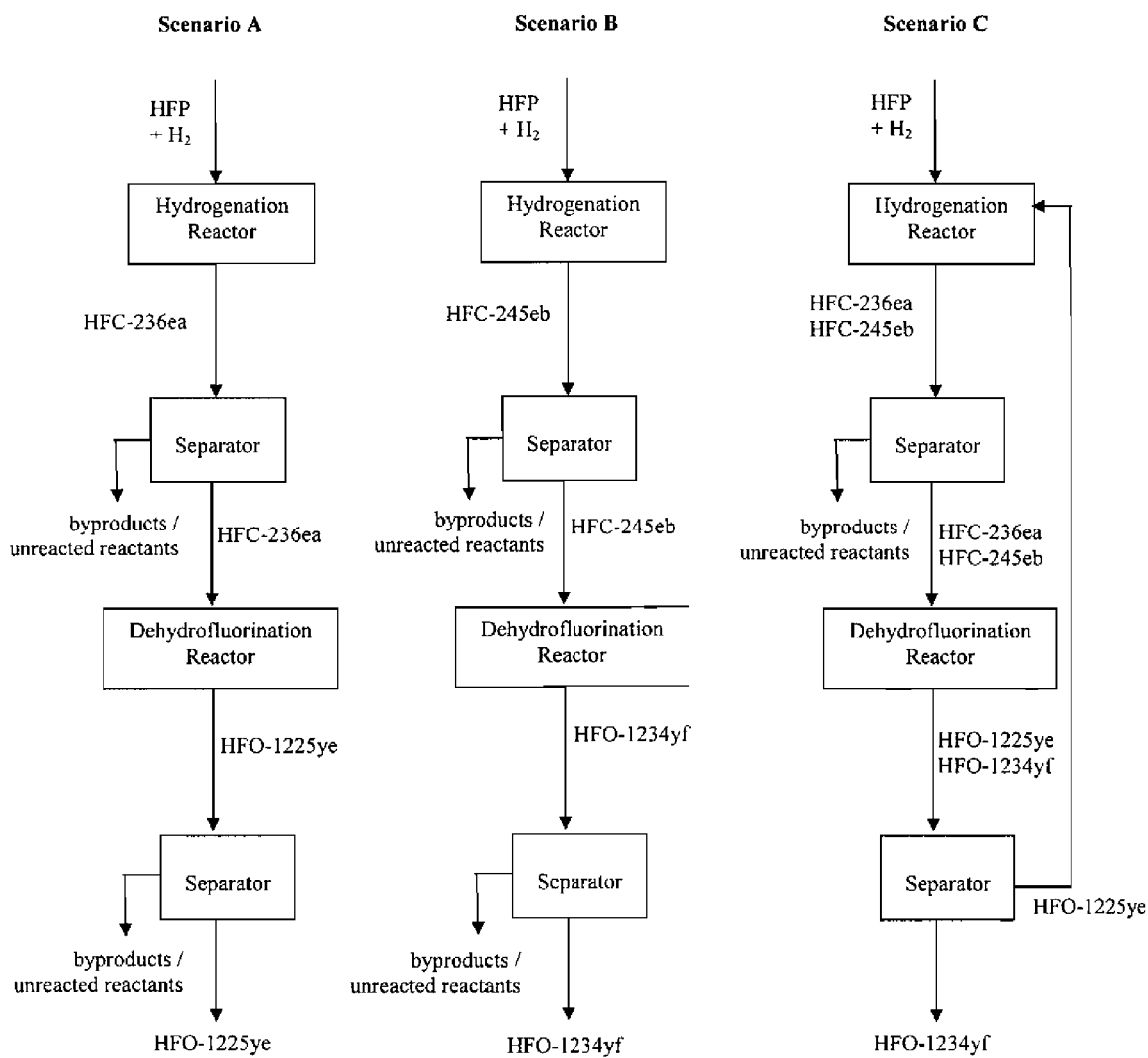
FIG. 10 is a process flow diagram showing the production of different fluoroolefins using the same four unit operations according to certain embodiments of the invention.

In an alternative embodiment, as illustrated in FIG. 9, separate separation trains may be used for the effluent from the dehydrohalogenation reaction step, especially when the feeds HFC-236ea and HFC-245eb are fed substantially separately into separate reaction trains.

What is claimed is:

1. A method for producing at least one fluorinated olefin comprising:
   a. hydrogenating a starting material stream comprising at least one alkene according to Formula (I):

$(CX_nY_{3-n})(CR^1_aR^2_b)_zCX=CH_mX_{2-m}$ (I)

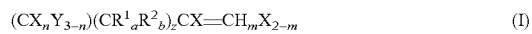

by contacting said starting material with a reducing agent to produce an intermediate product stream comprising at least one alkane according to Formula (II):

$(CX_nY_{3-n})(CR^1_aR^2_b)_zCHXCH_{m+1}X_{2-m}$ (II)

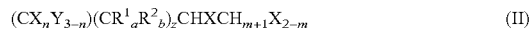

where:
   each X is independently Cl, F, I or Br, provided that at least two Xs are F;
   each Y is independently H, Cl, F, I or Br;
   each $R^1$ is independently H, Cl, F, I, Br or unsubstitued or halogen substituted methyl or ethyl radical;
   each $R_2$ is independently H, Cl, F, I, Br or unsubstitued or halogen substituted methyl or ethyl radical;
   n is 1, 2 or 3;
   a and b are each 0, 1 or 2, provided that a+b =2;
   m is 0, 1 or 2; and
   z is 0, 1, 2 or 3;
   b. optionally, separating said intermediate product stream into a plurality of stream, said plurality of intermediate product streams comprising two or more stream selected from the group consisting of a first stream rich in at least a first alkane according to Formula II, a seconds stream rich in at least a second alkane according to Formula II, and an alkane recycle stream;
   c. dehydrofluorinating at least a portion of said intermediate process stream from step (a) or said plurality of intermediate process streams of step (b) to produce an alkene product stream comprising 1,1,1,2,3-pentafluoropropene and at least one additional alkene having a lower degree of fluorine substitution compared to the degree of fluorination of the compound of formula (I);
   d. separating at least a portion of said 1,1,1,2,3-pentafluoropropene from said alkene product stream to produce a recycle stream rich in 1,1,1,2,3-pentafluoropropene and a final product stream rich in said additional alkene; and
   e. introducing said recycle stream at said step (a), wherein at least a portion of said 1,1,1,2,3-pentafluoropropene is hydrogenated to form a portion of said intermediate product stream.

2. The method of claim 1 wherein said additional alkene is a compound according to formula (III):

$(CX_nY_{3-n})(CR^1_aR^2_b)_zCX=CH_{m+1}X_{1-m}$ (III)

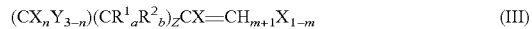

where each n is the same value as in formula (I) and m is 0 or 1.

3. The method of claim 2 wherein Z is 0.
4. The method of claim 3 wherein m is 0 or 1.
5. The method of claim 4 wherein said n is 3.
6. The method of claim 5 wherein X is F.
7. The method of claim 1 wherein said reducing agent is $H_2$.
8. The method of claim 1 wherein said starting material stream comprises hexafluoropropylene and said additional alkene is 1,1,1,2-tetrafluoropropene.

* * * * *